United States Patent [19]

Agrawal et al.

[11] Patent Number: 5,352,578
[45] Date of Patent: Oct. 4, 1994

[54] METHOD OF SEPARATING OLIGONUCLEOTIDES FROM A MIXTURE

[75] Inventors: Sudhir Agrawal; Paul C. Zamecnik, both of Shrewsbury, Mass.

[73] Assignee: Worcester Foundation for Experimental Biology, Shrewsbury, Mass.

[21] Appl. No.: 311,111

[22] Filed: Feb. 15, 1989

[51] Int. Cl.$^5$ ............ C12Q 1/68; C07H 21/00; C12N 15/00
[52] U.S. Cl. .................. 435/6; 536/25.3; 935/77; 935/78
[58] Field of Search ............ 435/6; 536/27, 25.3; 935/77, 78

[56] References Cited

U.S. PATENT DOCUMENTS 4,358,586  11/1982  Rubin .................. 536/24.31

FOREIGN PATENT DOCUMENTS

| | | |
|---|---|---|
| 0067597 | 12/1982 | European Pat. Off. . |
| 0192197 | 8/1986 | European Pat. Off. ............ 435/6 |
| 0221308 | 5/1987 | European Pat. Off. . |
| WI85/01051 | 3/1985 | World Int. Prop. O. . |

OTHER PUBLICATIONS

Aviv et al, Proceedings of the National Academy of Science, U. S. A., vol. 69, No. 6, pp. 1408-1412 (Jun. 1972).

Aviv and Leder, "Purification of Biologically Active Globin Messenger RNA by Chromatography on Oligothymidylic Acid–Cellulose", *Proc. Natl. Acad. Sci. USA,* 69: 1408–1412 (1972).

Okamura et al., "Purification of Terminal Deoxynucleotidyl-transferase by Olignoncleotide Affinity Chromatography", *J. Bio. Chem.*, 253: 3765–3767 (1978).

Thanki et al., "Selective Binding of Mouse Estradiol–Roceptor Complexes to Oligo(dT)–Cellulose," *J. Biol. Chem.* 253: 7744–7750 (1978).

Sheldon et al., "Detection o Polyadenylic Acid Sequences in Viral and Eukaryotic RNA", *Proc. Nat. Acad. Sci. USA,* 69: 417–421 (1972).

*Primary Examiner*—Mindy B. Fleisher
*Attorney, Agent, or Firm*—Allegretti & Witcoff, Ltd.

[57] ABSTRACT

A method of purifying full length synthetic target oligonucleotides from a mixture of oligonucleotides, particularly from a mixture containing truncated or failed sequences is disclosed. The method involves attaching a short nucleotide sequence complementary to the 5' end of a target oligonucleotide to a solid support. The complementarity between the most 5' nucleotides of the target oligonucleotide and the bound oligonucleotide results in hybridization which serves to retain the target oligonucleotide. Truncated or failed sequences lacking 5' sequences complementary to the attached oligonucleotide, fail to hybridize and therefore are not retained. The method makes it possible to purify gram quantities of synthetic deoxyribonucleic acids or ribonucleic acids and sequences which have modifications, such as on the phosphate backbone. The support-bound nucleotide sequences are stable under conditions of purification and therefore can be reused.

9 Claims, 6 Drawing Sheets

METHOD OF SEPARATING OLIGONUCLEOTIDES FROM A MIXTURE

FUNDING

This invention was made with government support under grant numbers A1-24846-03 and GM-21595-15 from the National Institutes of Health. The government has certain rights in the invention.

BACKGROUND OF THE INVENTION

Simple methods for synthesizing and purifying oligonucleotides are now in great demand due to the utility of synthetic oligonucleotides in a wide variety of molecular biological techniques. Automated synthesizers have proven useful in making targeted oligonucleotides. During oligonucleotide synthesis using an automated synthesizer, nucleotide monomers are progressively added to a nascent oligonucleotide chain. During each cycle, a percentage of the coupling reactions fail (i.e., no monomer addition occurs). Typically, coupling efficiency is 97–98% resulting in 2–3% of the reaction mixture being failed sequences. However, this error is multiplied as the oligonucleotide chain is lengthened. For example, in a typical 20-mer synthesis, the 20-mer product represents only 50–60% of the recovered oligonucleotide product. The remaining 40–50% represents failed sequences.

Since the chemical purity of a synthesized oligonucleotide is critical for any application, many techniques have been used to purify full length target nucleotides from truncated failed sequences. Among these are thin layer chromatography, polyacrylamide gel electrophoresis (PAGE), and high performance liquid chromatography (HPLC) by ion exchange using both normal and reversed phase modes. All of the aforementioned purification procedures can purify synthetic DNA only up to approximately 150 micrograms. In addition, all of these procedures require the reaction conditions to be varied if the phosphate backbone of the particular oligonucleotide has in any way been modified.

A method by which oligonucleotides having a desired sequence can be efficiently isolated in large quantities from a mixture of sequences, which includes failed sequences as well as sequences of interest, would be very useful.

SUMMARY OF THE INVENTION

The present invention relates to a method of separating (purifying) full length target oligonucleotides (i.e., nucleotide sequences containing the desired number of nucleotides) from a synthetic mixture of oligonucleotides, particularly from a mixture containing truncated failed sequences (i.e., nucleic acid sequences which have been produced by automated synthesis, but are less than the desired sequence). The method makes use of the fact that truncated failed sequences lack some of the nucleotides that are present at the 5' end of the full length target oligonucleotide.

Consider, for example, a full length 20-mer produced in a synthetic reaction 5'ACACCCAATTCTGAAAATGG3' and a failed sequence from the same synthetic reaction 5'AAAATGG3'. The 7 most 3' nucleotides of the failed sequence are identical in order and composition with those of the corresponding full length 20-mer. However, because extension of the failed sequence terminated following the addition of the 7th nucleotide in the chain, it lacks the 13 most 5' nucleotides. In order to isolate the desired 20-mer, the failed 7-mer as well as all of the other possible failed sequences (e.g., 8-mers, 9-mers, etc.) must be separated out.

In the method of the present invention, a short nucleotide sequence complementary to the 5' end of a target oligonucleotide is attached to a solid support. An oligonucleotide mixture resulting from a synthetic reaction is brought into contact with the attached oligonucleotide in an appropriate vessel under conditions which promote hybridization of complementary nucleotide sequences. The complementarity between the most 5' nucleotides of the target oligonucleotide and the monomer units of the attached oligonucleotide results in the formation of hydrogen bonds which serve to retain the target oligonucleotide in the reaction vessel, whereas truncated failed sequences lacking 5' sequences complementary to the attached oligonucleotide pass through the reaction vessel. The target oligonucleotides are subsequently recovered by known methods such as contacting them with an eluting solution under conditions tending to disrupt intermolecular hybridization.

The present method can also be used to separate target oligonucleotides from any mixture, such as that resulting from fragmentation of nucleic sequences using restriction enzymes or mechanical means.

A useful advantage of this invention over the presently available methods is that using the present method, microgram to gram quantities of target nucleotide sequences can be purified. In addition, any synthetic oligonucleotide (deoxy- or ribo-), including those which mimic naturally-occurring sequences and those which have modifications, such as on the phosphate backbone, can be purified using this method.

A further advantage is that the support-bound nucleotide sequences are stable under conditions of purification and, therefore, can be reused. In addition, the purity of the isolated oligonucleotide is estimated to be 98%, and essentially no synthetic target oligonucleotides are lost. A final advantage is that this method does not require the use of potentially carcinogenic organic solvents.

The above and other features of the invention including various novel details of construction and combinations of parts will now be more particularly described with reference to the accompanying drawings and pointed out in the claims. It will be understood that the particular method of oligonucleotide purification embodying the invention is shown by way of illustration only and not as a limitation of the invention. The principles and features of this invention may be employed in varied and numerous embodiments without departing from the scope of the invention.

DETAILED DESCRIPTION OF THE INVENTION

The present invention relates to a method for purifying full length target oligonucleotides of any length but generally between 5 to 50 nucleotides from a synthetic reaction product mixture containing truncated or failed sequences. The oligonucleotide sequences can be oligoribonucleotide or oligodeoxyribonucleotide sequences. Both types are referred to herein as oligonucleotides. The method makes use of the fact that truncated or failed sequences lack some of the nucleotides that are present at the 5' end of the full-length target oligonucleotide.

In the method of the subject invention, an oligonucleotide complementary to the 5' end of the full length target oligonucleotide (i.e., an oligonucleotide of preselected size and sequence) is attached (e.g., covalently bonded) to a solid support medium (e.g., glass beads, polystyrene, cellulose, agarose, Sephadex, Sepharose, paper, etc.) in a reaction vessel (e.g., column), as described in greater detail in Examples 1 and 2, or by using any one of a number of known techniques (R. T. Pon, *Biotechniques* 6: 8 (1988) and references therein).

Figure 1A:
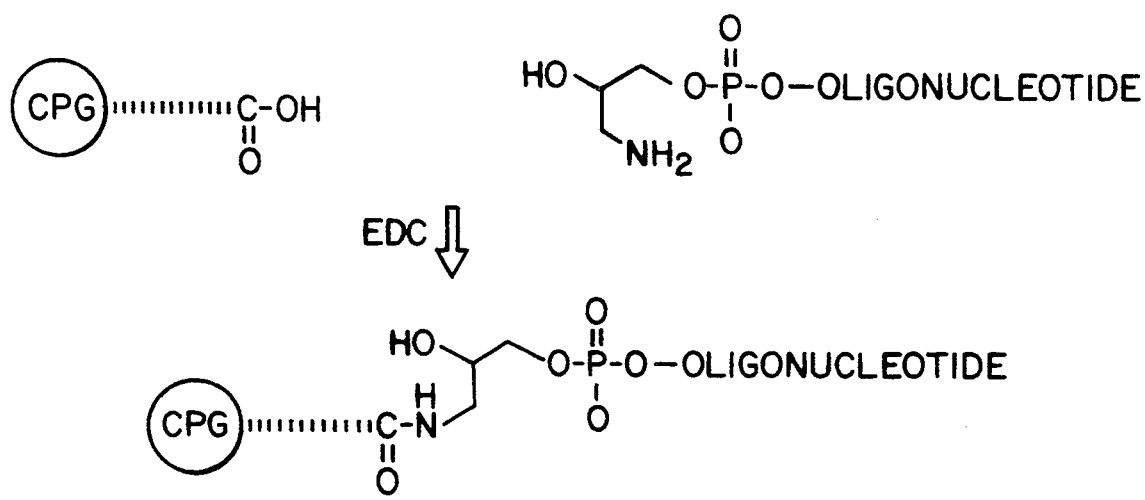
FIGS. 1A, 1B, 1C, and 1D shows chemistry for four methods of attaching nucleotide sequences to a solid support.

FIG. 1(a) illustrates the attachment of a 3' end-derivatized oligonucleotide sequence to a —COOH derivatized support (e.g., CPG) in the presence of water soluble carbodiimide EDC. FIGS. 1(c) and 1(d) illustrate methods of synthesizing oligonucleotides on a ribonucleoside support and then attaching the oligonucleotides to the support either by derivatizing the 3' end of the oligonucleotide by forming an amino group that can be reacted with carboxyl-derivatized support (1(c)) or by reacting the dialdehyde on the 3' end of the oligonucleotide directly with $NH_2$-derivatized CPG (1(d)).

Alternatively, the sequence complementary to the target oligonucleotide can be synthesized directly on the solid support, if the linkages are stable in acidic and basic conditions. This is described in greater detail in Example 3.

Figure 1B:
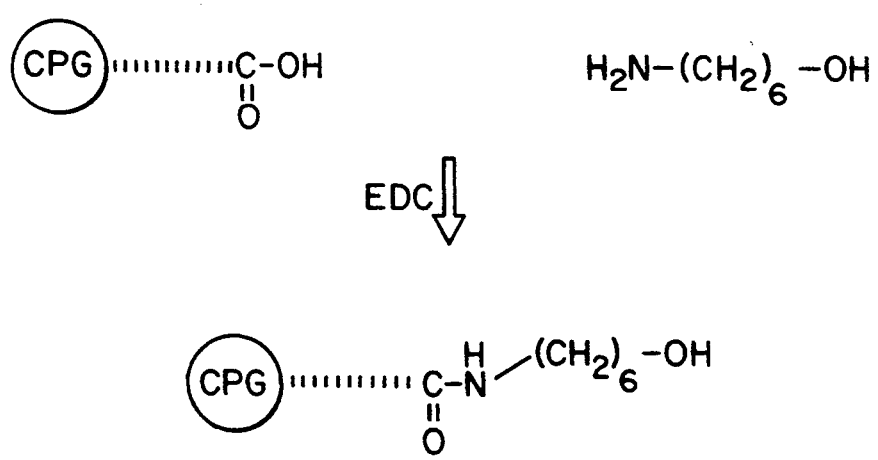
Figure 1C:
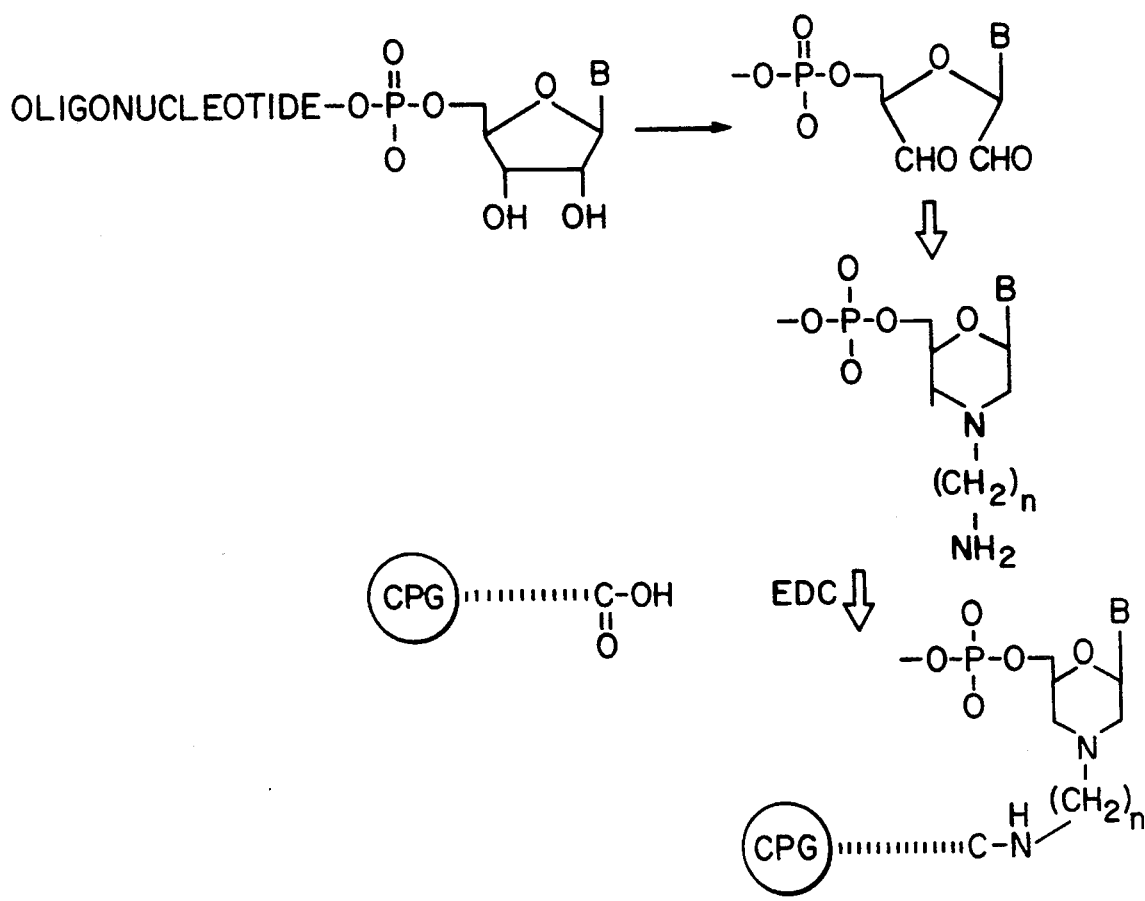
Figure 1D:
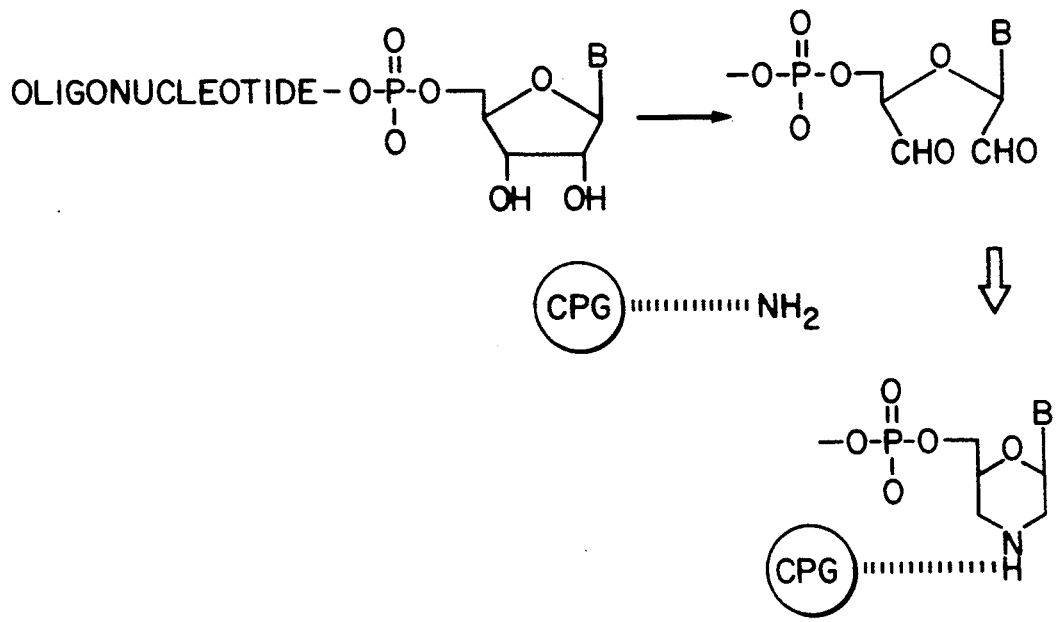

FIG. 1(b) illustrates the reaction of carboxyl derivatized support with aminohexanol in the presence of EDC to form a hydroxyl-derivatized support which can be used to assemble oligonucleotides.

The sequence complementary to the 5' end of the target oligonucleotide sequence is referred to herein as the attached oligonucleotide. A reaction vessel (e.g., column) is then primed by passing through it a quantity of hybridization solution (e.g., buffer) sufficient to thoroughly saturate the solid support medium and the attached oligonucleotide.

Figure 2:
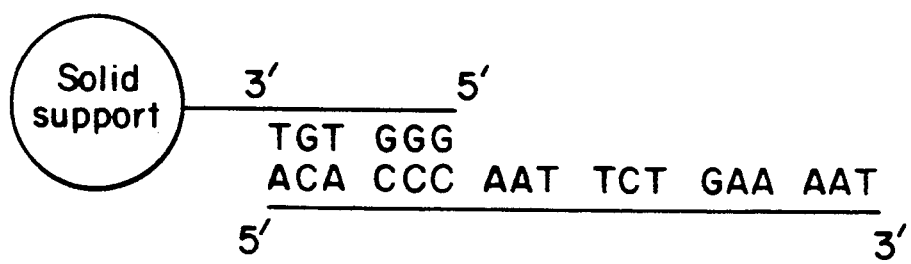
FIG. 2 is a schematic representation of a support-bound hexamer sequence hybridized to the 5' end of a target oligonucleotide.
Figure 3:
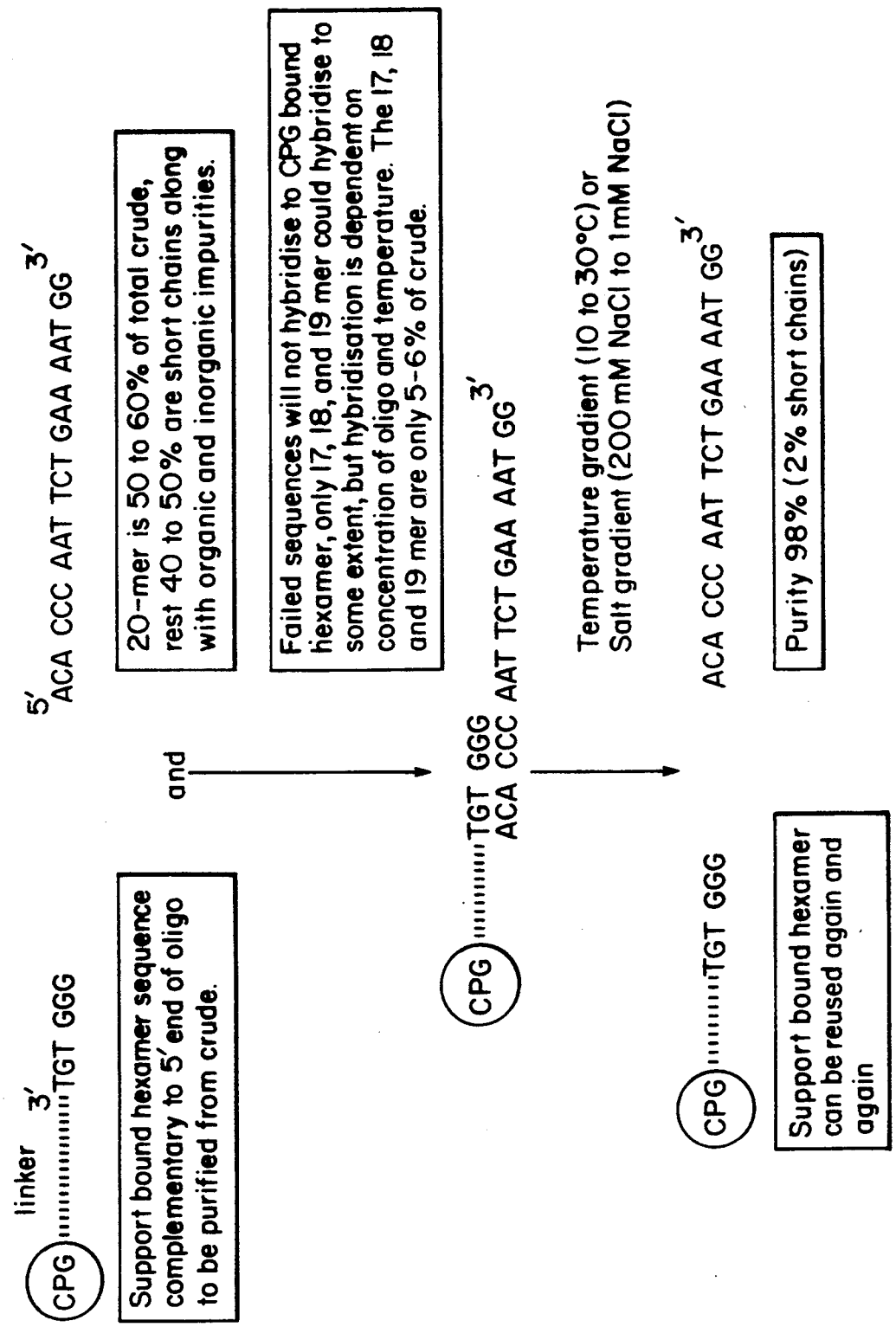
FIG. 3 is a schematic representation of the purification scheme of the present invention.

The synthetic reaction products are recovered from the solution and resuspended in hybridization solution. The resuspended reaction mixture is then passed through the reaction vessel. Full length target oligonucleotides form hydrogen bonds (i.e., hybridize) with the attached oligonucleotide and are retained in the reaction vessel. Truncated failed sequences, which cannot form any or a sufficient number of hydrogen bonds to remain bound to the attached oligonucleotides under the elution conditions, pass with the flow out of the reaction vessel. This method is described in greater detail in Example 4. FIG. 2 depicts the attached oligonucleotide hybridized to the target oligonucleotide. FIG. 3 schematically illustrates the purification scheme.

There may be a class of truncated failed sequences which share a degree of complementarity with the linked oligonucleotide. Consider, for example, an attached hexamer used to isolate a full-length target oligonucleotide which is a 20-mer present in a synthetic reaction mixture. Assuming 97-98% coupling efficiency at each monomer addition step, 6-9 % of the crude synthetic reaction product mixture represents oligonucleotides with extension failures following the addition of the 17th, 18th, or 19th nucleotide. These three truncated failed sequences will form hydrogen bonds with the linked oligonucleotide because these failed sequences have 5' ends which are complementary with at least a portion of the attached oligonucleotide. However, the degree of bonding between these failed sequences and the attached oligonucleotide will vary depending upon the extent of complementarity (i.e., the number of bases that hydridize with the affixed oligonucleotide). For example, a synthetic nucleotide sequence which has failed to extend following the addition of the 19th nucleotide will form a stronger bond with the attached oligonucleotide than would a nucleotide sequence which has failed to extend following the addition of the 18th nucleotide.

Oligonucleotides retained in the reaction vessel are released in an elution step described in greater detail in Examples 5 and 6. For example, the passage of a salt gradient (e.g., 200 mM to 1 mM NaCl) through the reaction vessel or a gradient in temperature (e.g., 5° C. to 40° C.) reduces the hydrogen bonding potential of the nucleic acids. Because the hydrogen bonding potential of the nearly full length failed sequences is less than that of the full length target oligonucleotide, the former will be released from the reaction vessel earlier than the latter. FIG. 3 depicts schematically the purification scheme of the subject invention.

Figure 4:
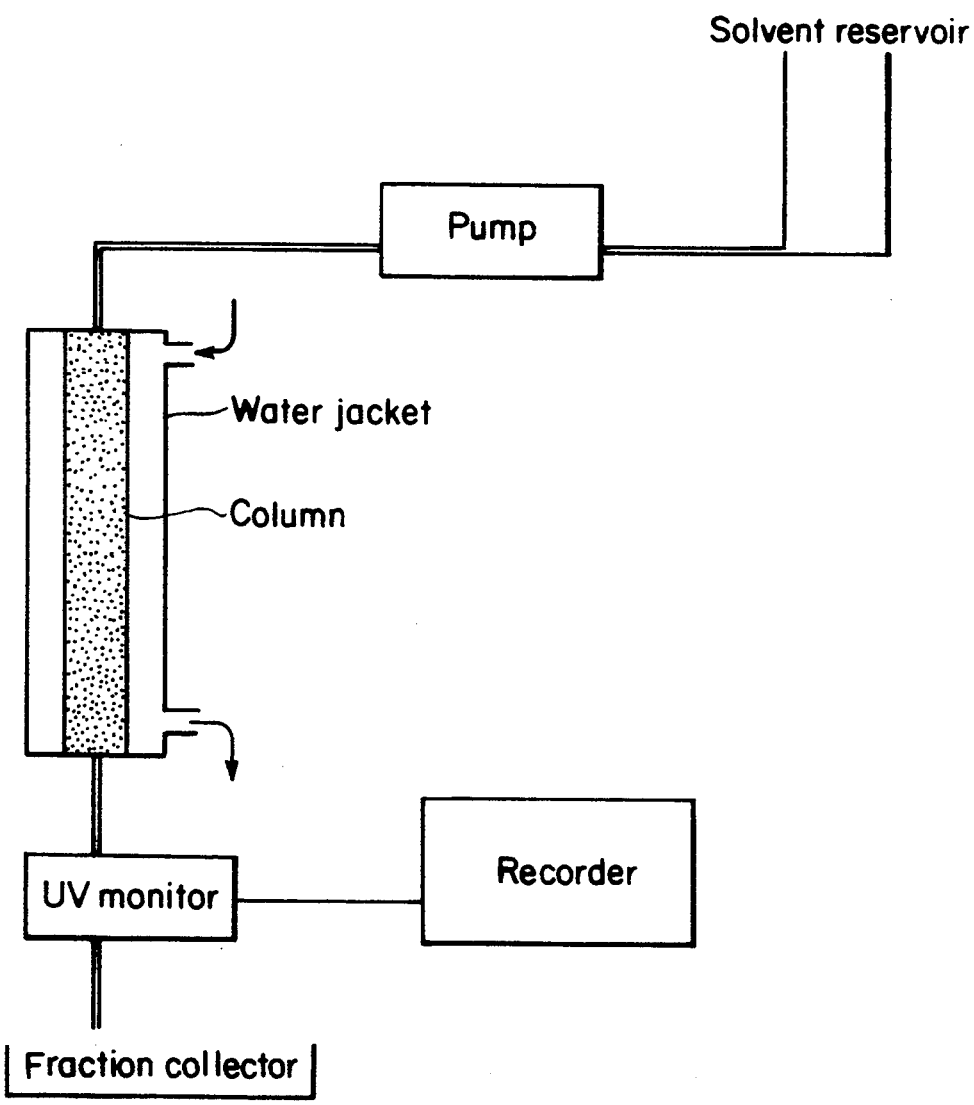
FIG. 4 is a flow chart diagram of an instrument which can be used in the purification method of the present invention.

FIG. 4 illustrates an instrument which can be used in the present method of purification. The crude mixture is poured into the solvent reservoir and pumped into the column. Once in the column, the target oligonucleotides hybridize with attached oligonucleotides in the column. If elution is to be accomplished via a salt gradient, the salt buffer is poured into the solvent reservoir. If elution is to be accomplished via a temperature gradient, the temperature within the column is increased by raising the temperature of the water in the surrounding water jacket. The UV monitor and recorder are useful in detecting the final elution product, the target oligonucleotides from the almost full-length, failed sequences.

Figure 5:
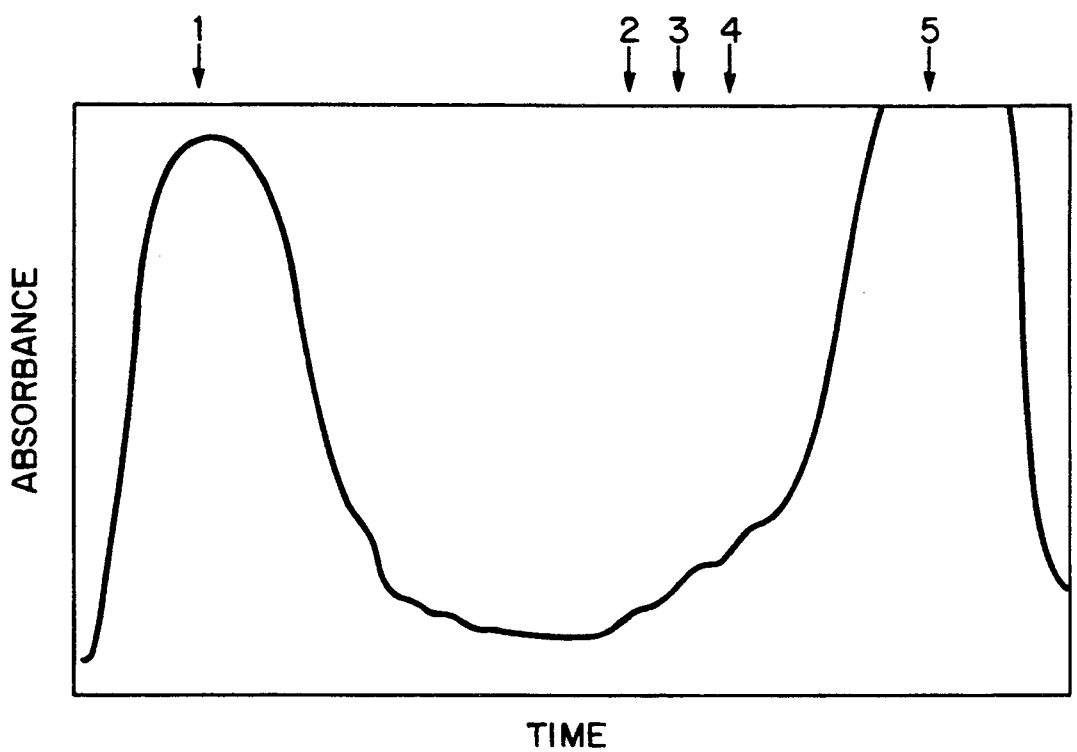
FIG. 5 is a recording for the elution of synthetic oligonucleotides using the purification method of the present invention.

FIG. 5 is a typical recording of the purification of synthetic oligonucleotides using the method of the subject invention. The first peak (1) contains the short sequences which are not hybridized and therefore come straight off the column with the first application of buffer. After washing all the unhybridized sequences, hybridized sequences are eluted by a thermal or salt gradient. Peaks (2), (3) and (4) are n-3, n-2 and n-1 (i.e., almost full length but failed sequence) peaks. Peak (5) is the target nucleotide. For example, if Peak (5) represents a 20-mer, Peak (2), (3) and (4) are 17-mers, 18-mers and 19-mers, respectively.

Figure 6:
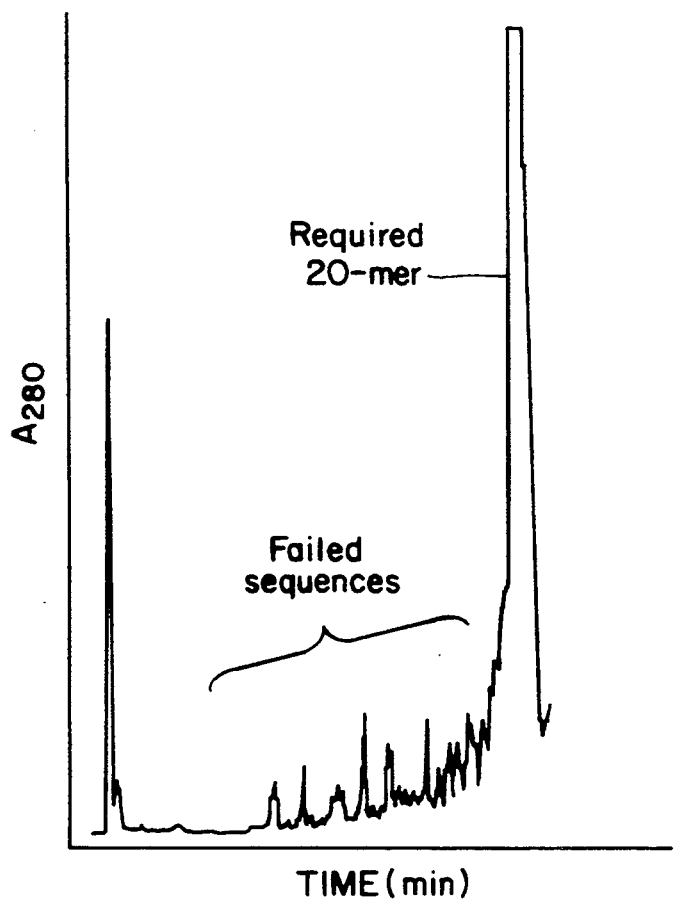
FIG. 6 shows the HPLC profile of a crude 20-mer synthetic product reaction mixture.
Figure 7:
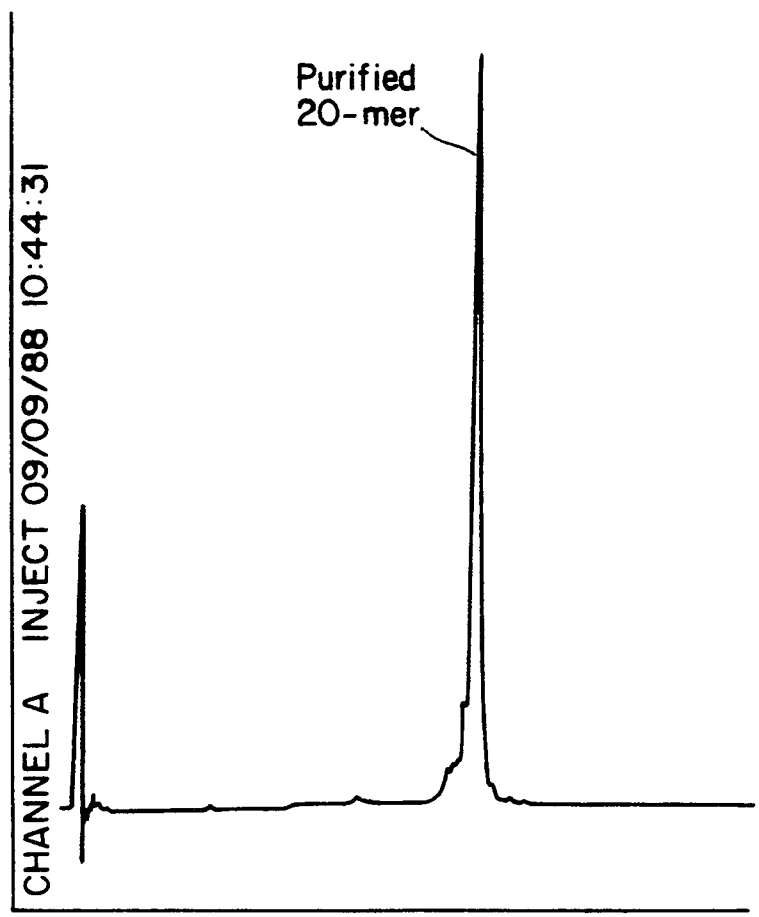
FIG. 7 shows the HPLC profile of a 20-mer synthetic product purified using the method of the subject application.

FIG. 6 is the ion exchange h.p.l.c. profile of a crude 20-mer (i.e., containing target and failed oligonucleotides), and FIG. 7 is the ion exchange h.p.l.c. profile of a 20-mer purified by the method of the subject invention. An example of the HPLC conditions is described in Example 7. As can be seen in FIG. 7, the unhybridized failed sequences elute early on and the almost full-length sequences elute upon application of a gradient (e.g., a salt or thermal gradient), while in FIG. 6, a number of failed sequences are evident throughout. Clearly the subject invention is a useful method in purifying target oligonucleotide sequences from failed sequences.

An important feature of this invention is that it is also useful for purification of modified oligonucleotides (i.e., polymers of nucleotide monomers having different 3'-5' internucleotide bonds (e.g., phosphorothioates, methyl phosphonates, phosphoramidates and phosphotriesters). For example, one is able to use the H-phosphonate method of synthesizing DNA, oxidize the H-phosphonate intermediate to yield one or more modifications of the phosphate backbone and then use the method of the present invention to purify a large quantity of the modified oligonucleotide.

Figure 8:
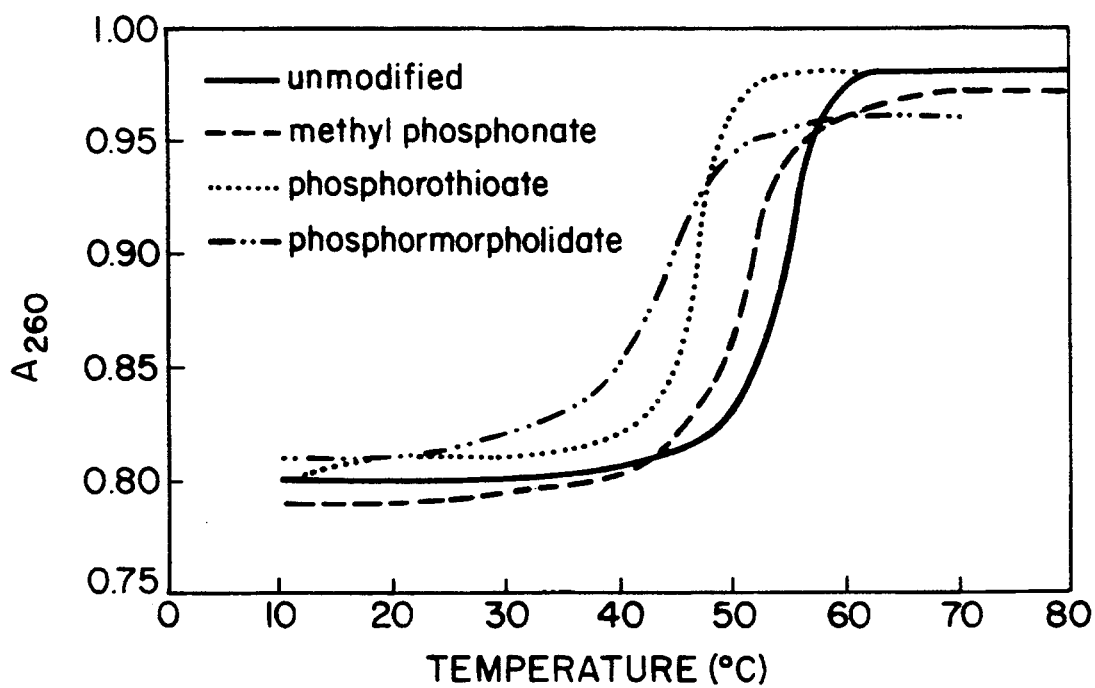
FIG. 8 shows the melting temperature curve for four different backbone modified oligonucleotides.

FIG. 8 shows melting temperature curves for three different phosphate backbone modified oligonucleotides (methylphosphonate, phosphorothioate, phosphormorpholidate) and for an unmodified oligonucleotide. The sequences are 20-mers hybridized to a complementary 20-mer in 100 mM NaCl (pH 7.4). As evidenced in the curves, each oligonucleotide hybridized to its complementary sequence and the melting temperature, indicating the temperature at which the hybridized sequence separate, was in the range of 44°–55°. When these sequences are hybridized to 5 or 6-mers, the melting temperature is only to 15°–25°, but hybridization is still base specific.

The present invention will now be further illustrated by the following examples, which are not intended to be limiting in any way.

EXAMPLE 1

Attaching Unprotected, Derivatized Oligonucleotides to Reactive Solid Support Surfaces 3'-Amino derivatized oligonucleotides were assembled using a special linker as shown in FIG. 1(a). After the assembly and following a deprotection step, the amino oligonucleotide was attached to the carboxyl-derivatized CPG in the presence of triethylamine, anhydrous pyridine, dimethylaminopyridine as a catalyst and 1-(3-dimethylaminopropyl)-3-ethylcarbodiimide (EDC, sometimes called 1-ethyl-3(3-dimethylaminopropyl)carbodimide (Chu, B. C. F., *Proc. Natl. Acad. Sci, USA*, 82: 963–967 (1985); HO, M. W. Y., Duncan, R. E. and B. T. Gilham, *Biochem* 20: 64–67 (1981)).

The reaction mixture was sonicated for 2 minutes and then stirred for 24 hours. The solid support was then washed with pyridine followed by acetonitrile, and ether, then dried.

EXAMPLE 2

Attachment of Oligonucleotides to Solid Support Through Dialdyhyde Route

Synthesis of the required sequence was carried out on a ribonucleoside support. After the assembly and deprotection step of Example 1, the 2', 3' cisdiol was oxidized with sodium metaperiodate to yield a dialdehyde which in turn was reacted with 1,6-diaminohexane and reduced with sodium cyanoborohydride. The amino group was then reacted with the carboxyl derivatized support in the presence of EDC as reported by Agrawal, S., *Nucl. Acid. Res.*, 14,15: 6227–6247 (19) and illustrated in FIG. 1(c). Alternatively, the dialdehyde can be directly reacted with $NH_2$-derivatized CPG as illustrated in FIG. 1(d).

Example 3

Synthesizing Oligonucleotide on Solid Support

Carboxyl-derivatized support was reacted with aminohexanol in the presence of EDC, as mentioned in Example 1. After the reaction, the support was washed and dried. The hydroxyl-derivatized support as shown in FIG. 1(b) was then used for assembling oligonucleotide sequences. After the assembly, the support was deprotected. As all the linkages in between the oligonucleotide and the support are resistant to acid or base hydrolysis, the oligonucleotide remains attached.

EXAMPLE 4

Hybridization of Target Oligonucleotides to Complementary Support-Bound Sequences After all deprotection steps (e.g., ammonia to remove base protecting groups), the crude mixture of synthetic oligonucleotide is taken up in water. 400 mM NaCl solution was then mixed with the crude aqueous solution of oligonucleotide so that the resulting overall concentration of NaCl was 200 mM. This solution was loaded onto the column either manually or by injection. The concentration of crude oligonucleotide varies depending on the amount of impurities, size of the column, and the amount of attached oligonucleotide loaded on the solid surface. For example, if loading is 12 umole/g$^{-1}$, 12 um of 20-mer oligonucleotide can be purified. 1 gram of CPG has a bed volume of about 2 ml, so that 20 uM of crude oligonucleotide (which includes about 12 uM of pure oligonucleotide is about 72 mg), can be dissolved in 3 ml of salt buffer. The crude oligonucleotide was passed through the column at a flow rate of 0.2 ml/min for 15 mins. During this flow, the temperature of the column was lowered to 5° to 10° C., depending on the phosphate backbone. After 15 minutes, the support was cooled to 5° C.

EXAMPLE 5

Elution of Oligonucleotide Using Salt Gradient

After 5° C., the support was washed with 200 mM salt buffer solution. Elution was recorded by a UV monitor. After washings with a gradient ranging from 200 mM to 1 mM NaCl, the last peak as detected by the UV monitor was collected.

EXAMPLE 6

Elution of Oligonucleotide Using Thermal Gradient

At 5° C., the support was washed with a 200 mM salt buffer solution. Elution was recorded by a UV monitor. The temperature was then slowly raised to 40° C. in a linear fashion. The last peak as detected on the UV monitor was collected.

EXAMPLE 7

H.P.L.C. Conditions

H.P.L.C. was carried out using a Water's 600E system controller, Lambda max 481 LC Spectrophotometer, Water's 745 Data Module and Whatman Partisphere SAX column. Buffers used were; (A) 1 mM $KH_2PO_4$ (pH 6.3)/60% $HCONH_2$ and (B) 300 mM $KH_2PO_4$ (pH 6.3)/60% $HCONH_2$. The gradient run was 0% B for 2 minutes, then 0–80% B in A and B over 30 minutes. The flow rate was 2 ml $min^{-1}$ and the detector was set at 280 nm Absorbance.

Utility

The present invention is for an improved method of purifying oligonucleotides in microgram to gram quantities. The method is useful in providing purified oligonucleotides and, thus, is of value to at least the following basic and applied molecular biological techniques employing synthetic oligonucleotides. In "gene screening," synthetic oligonucleotides having a nucleotide sequence complementary to a gene or mRNA of interest are labeled with a reporter group and used to detect the presence of that gene or mRNA in a cDNA or a genomic DNA library.

Synthetic oligonucleotides are also frequently employed as primers for reverse transcriptase in procedures for synthesizing DNA from a single stranded RNA template. In addition, synthetic oligonucleotides can be used to create specific mutations in a cDNA segment, which can then be reintroduced into the organism to observe the changes in the organism resulting from the mutation. This technique is a noteworthy advance over the classical approach of creating in vivo mutations randomly throughout the genome and then isolating those that display a particular phenotype.

Finally, synthetic oligonucleotides (modified or unmodified) are useful as antiviral agents. For example, an antisense oligonucleotide which is complementary to a portion of a viral mRNA molecule is synthesized, using known techniques. The antisense oligonucleotide is then introduced into the virus so that it hybridizes with the complementary region of the mRNA in the virus to form a double stranded region. This double stranded region of the viral mRNA cannot be translated. A large amount of synthetic oligonucleotide is required for this purpose (e.g., grams). Thus, the method of the subject invention which can purify large quantities of oligonucleotides has special importance for this application.

In addition, unlike presently-available methods of purifying DNA, the method of the subject invention does not require reaction conditions to be varied for modified oligonucleotides. Modified synthetic oligonucleotides have a variety of applications. Phosphorothioate DNA analogs that bear a sulfur in the internucleoside linkage are currently being used as nuclease-resistant anti-sense oligonucleotides either for blocking translation or inhibiting viral DNA synthesis. Marcus-Sekura, C. J. et al. *Nucl. Acid Res* 15: 5749–5763 (1987); Agrawal, S. et al., *Proc. Natl Acad. Sci. USA*, 85: 7079–7083 (1988). In the past, phosphorothioates have been used to study the stereochemistry of restriction endonucleases (Matsukura, M. et al. *Proc. Nat. Acad. Sci. USA* 84: (1987); Stec, W. J. et al., *J. Amer. Chem. Sco.* 106: Connolly, B. A. et al., *Biochem* 23: 3443–3453 (1984)), the structural dynamics of DNA (Koziolkiewicz, M et al., *Phosphorus and Sulfur* 27: 81–92 (1986)), recognition of DNA by proteins (e.g., monoclonal, anti-native DNA antibodies, LaPlanche, C. A. et al., *Nucl. Acid. Res.* 14: 9081–9093 (1986)), and to elucidate certain enzyme mechanisms, including protein-nucleic acid interactions (Porter, B. and F. Eckstein, *J. Biol. Chem.* 259: 14243 (1984).

Methyl phosphonate analogues of DNA have increased hydrophobicity and have been shown to pass readily through cell membranes and inhibit protein synthesis, presumably by interfering with mRNA translation. Blake, K., et al., *Biochem* 24: 6139 (1985); Smith, C. et al., *Proc. Natl. Acad. Sci USA* 83: 2787 (1986); Agrawal, S. et al., *Tet. Lett.*, 28: 3539–3542 (1987); Sarin, P. S. et al., *Proc. Natl. Acad. Sci. USA*, 85: 7448–7451 (1988).

Phosphoramidate analogues of dinucleotides are known to bind to complementary polynucleotides and have been used for the attachment of various ligands to DNA. Letsinger, R. et al., *Nucl. Acids Res.* 14: 3487 (1986); Agrawal, S. et al., *Proc. Natl. Acad. Sci. USA*, 85: 7079–7083 (1988).

All of the aforementioned basic and applied molecular biological techniques employing synthetic oligonucleotides will benefit from the method of the subject invention, whereby synthetic oligonucleotides can be purified in gram quantities and the reaction conditions do not have to be varied for modified oligonucleotides.

Equivalents

Those skilled in the art will recognize or be able to ascertain using no more than routine experimentation, many equivalents to the specific embodiments of the invention described herein. These and all other equivalents are intended to be encompassed by the following claims.

We claim:

1. A method of separating full length target oligonucleotides from failed sequences in an oligonucleotide mixture resulting from an oligonucleotide synthesis reaction, the method comprising the steps of:
   a. covalently binding short oligonucleotides having nucleotide sequences complementary to the 5' end of the full length target oligonucleotides to a solid support, thereby producing covalently bound oligonucleotides;
   b. contacting the covalently bound oligonucleotides and the oligonucleotide mixture resulting from an oligonucleotide synthesis reaction under conditions appropriate for hybridization of complementary nucleotide sequences resulting in hybridization of covalently bound oligonucleotides with full length target oligonucleotides and with nearly full length failed oligonucleotides;
   c. subjecting the hybridized products of (b) to a gradient appropriate for disrupting the hybridization of covalently bound oligonucleotides with nearly full length failed oligonucleotides, but not for disrupting the hybridization of covalently bound oligonucleotides with full length target oligonucleotides;
   d. recovering full length target oligonucleotides by subjecting the covalently bound oligonucleotide-target oligonucleotide products remaining in (c) to conditions appropriate for disrupting by hybridization.

2. The method of claim 1 wherein the full length target oligonucleotides and the attached oligonucleotides are oligodeoxynucleotides.

3. The method of claim 1, wherein the covalently bound oligonucleotides are 5–10 bases in length.

4. The method of claim 1 wherein the full length target oligonucleotides are modified oligonucleotides and the modification occurs in a portion of the full length target oligonucleotides other than that portion complementary to the attached oligonucleotides.

5. The method of claim 4 wherein the modified oligonucleotides are selected from the group consisting of:
   a. oligonucleotide methylphosphonate,
   b. oligonucleotide phosphorothioate,
   c. oligonucleotide phosphoramidate,
   d. oligoribonucleotide and phosphate backbone analogs thereof,
   e. equivalents thereof, said equivalents being nucleotide sequences which are sufficiently similar in sequence at the 5' end to the full length target oligonucleotides to be capable of hybridizing with the attached oligonucleotides.

6. The method of claim 1 wherein the gradient of step (c) is a salt gradient.

7. The method of claim 1 wherein the gradient of step (c) is a temperature gradient.

8. The method of claim 1 wherein microgram to gram quantities of full length target oligonucleotides are separated from a synthetic mixture of oligonucleotides.

9. The method of claim 1 wherein the attached oligonucleotide is a modified oligonucleotide.

* * * * *